(12) United States Patent
Colleran

(10) Patent No.: US 8,267,997 B2
(45) Date of Patent: Sep. 18, 2012

(54) VERTEBRAL INTERBODY COMPRESSION IMPLANT

(75) Inventor: Dennis Colleran, North Attleboro, MA (US)

(73) Assignee: Theken Spine, LLC, Akron, OH (US)

( * ) Notice: Subject to any disclaimer, the term of this patent is extended or adjusted under 35 U.S.C. 154(b) by 799 days.

(21) Appl. No.: 12/269,550

(22) Filed: Nov. 12, 2008

(65) Prior Publication Data

US 2009/0265007 A1   Oct. 22, 2009

Related U.S. Application Data

(60) Provisional application No. 60/987,111, filed on Nov. 12, 2007.

(51) Int. Cl.
*A61F 2/44* (2006.01)
(52) U.S. Cl. .................................................. 623/17.11
(58) Field of Classification Search .............. 623/17.11
See application file for complete search history.

(56) References Cited

U.S. PATENT DOCUMENTS

| | | |
|---|---|---|
| 1,503,124 A | 7/1924 | Hoppes |
| 1,824,739 A | 9/1931 | Johnson et al. |
| 4,599,086 A | 7/1986 | Doty |
| 5,059,193 A | 10/1991 | Kuslich |
| 5,171,278 A | 12/1992 | Pisharodi |
| 5,306,309 A | 4/1994 | Wagner et al. |
| 5,336,223 A | 8/1994 | Rogers |
| 5,431,658 A | 7/1995 | Moskovich |
| 5,484,437 A | 1/1996 | Michelson |
| 5,522,899 A * | 6/1996 | Michelson ............... 606/279 |
| 5,593,409 A | 1/1997 | Michelson |
| 5,609,635 A | 3/1997 | Michelson |
| 5,653,762 A | 8/1997 | Pisharodi |
| 5,658,335 A | 8/1997 | Allen |
| 5,658,336 A | 8/1997 | Pisharodi |
| 5,665,122 A | 9/1997 | Kambin |
| 5,683,394 A | 11/1997 | Rinner |
| 5,683,464 A | 11/1997 | Wagner et al. |
| 5,702,455 A | 12/1997 | Saggar |
| 5,722,977 A | 3/1998 | Wilhelmy |
| 5,741,253 A | 4/1998 | Michelson |
| 5,749,916 A | 5/1998 | Richelsoph |
| 5,782,830 A | 7/1998 | Farris |
| 5,782,832 A | 7/1998 | Larsen et al. |
| 5,797,909 A | 8/1998 | Michelson |
| 5,800,547 A | 9/1998 | Schafer et al. |
| 5,861,041 A | 1/1999 | Tienboon |
| 5,865,845 A | 2/1999 | Thalgott |
| 5,885,299 A | 3/1999 | Winslow et al. |

(Continued)

FOREIGN PATENT DOCUMENTS

EP    1104665    6/2001

(Continued)

*Primary Examiner* — Bruce E Snow
(74) *Attorney, Agent, or Firm* — Middleton Reutlinger; Robert H. Eichenberger; Chad D. Bruggeman

(57) ABSTRACT

An apparatus and method for securing boney structures is disclosed which includes a compression mechanism and a force transfer mechanism. The compression mechanism may have bone engagement members that have one portion slideably coupled to a housing positioned within the implant and another portion rotatably coupled to the implant so that a movement of the housing causes the slideable portion to move within the housing and a penetrating member to rotate about the rotatably coupled portion. The force transfer mechanism may be coupled to the compression mechanism to move the housing.

17 Claims, 11 Drawing Sheets

U.S. PATENT DOCUMENTS

| | | |
|---|---|---|
| 5,888,227 A | 3/1999 | Cottle |
| 5,888,228 A | 3/1999 | Knothe et al. |
| 5,899,901 A | 5/1999 | Middleton |
| 5,944,658 A | 8/1999 | Koros et al. |
| 5,976,187 A | 11/1999 | Richelsoph |
| 5,980,522 A | 11/1999 | Koros et al. |
| 6,017,342 A | 1/2000 | Rinner |
| 6,030,390 A | 2/2000 | Mehdizadeh |
| 6,042,582 A | 3/2000 | Ray |
| 6,045,579 A | 4/2000 | Hochshuler et al. |
| 6,063,088 A | 5/2000 | Winslow |
| 6,066,175 A | 5/2000 | Henderson et al. |
| 6,080,155 A | 6/2000 | Michelson |
| 6,080,193 A | 6/2000 | Hochshuler et al. |
| 6,083,225 A | 7/2000 | Winslow et al. |
| 6,083,228 A | 7/2000 | Michelson |
| 6,096,038 A | 8/2000 | Michelson |
| 6,102,949 A | 8/2000 | Biedermann et al. |
| 6,102,950 A | 8/2000 | Vaccaro |
| 6,113,638 A | 9/2000 | Williams et al. |
| 6,113,639 A | 9/2000 | Ray et al. |
| 6,123,705 A | 9/2000 | Michelson |
| 6,126,689 A | 10/2000 | Brett |
| 6,136,031 A | 10/2000 | Middleton |
| 6,156,037 A | 12/2000 | LeHuec et al. |
| 6,159,211 A | 12/2000 | Boriani et al. |
| 6,159,215 A | 12/2000 | Urbahns et al. |
| 6,159,244 A | 12/2000 | Suddaby |
| 6,159,245 A | 12/2000 | Meriwether et al. |
| 6,174,334 B1 | 1/2001 | Suddaby |
| 6,179,873 B1 | 1/2001 | Zientek |
| 6,183,517 B1 | 2/2001 | Suddaby |
| 6,193,755 B1 | 2/2001 | Metz-Stavenhagen et al. |
| 6,193,757 B1 | 2/2001 | Foley et al. |
| 6,200,348 B1 | 3/2001 | Biedermann et al. |
| 6,206,922 B1 | 3/2001 | Zdeblick et al. |
| 6,224,599 B1 | 5/2001 | Baynham et al. |
| 6,224,607 B1 | 5/2001 | Michelson |
| 6,235,059 B1 | 5/2001 | Benezech et al. |
| 6,245,108 B1 | 6/2001 | Biscup |
| 6,251,140 B1 | 6/2001 | Marino et al. |
| 6,261,296 B1 | 7/2001 | Aebi et al. |
| 6,267,763 B1 | 7/2001 | Castro |
| 6,270,498 B1 | 8/2001 | Michelson |
| 6,277,122 B1 | 8/2001 | McGahan et al. |
| 6,283,966 B1 | 9/2001 | Houfburg |
| 6,290,724 B1 | 9/2001 | Marino |
| 6,302,914 B1 | 10/2001 | Michelson |
| 6,319,257 B1 | 11/2001 | Carignan et al. |
| 6,332,887 B1 | 12/2001 | Knox |
| 6,332,895 B1 | 12/2001 | Suddaby |
| 6,364,880 B1 | 4/2002 | Michelson |
| 6,371,987 B1 | 4/2002 | Weiland et al. |
| 6,409,766 B1 | 6/2002 | Brett |
| 6,419,705 B1 | 7/2002 | Erickson |
| 6,423,095 B1 | 7/2002 | Van Hoeck et al. |
| 6,428,541 B1 | 8/2002 | Boyd et al. |
| 6,428,544 B1 | 8/2002 | Ralph et al. |
| 6,432,106 B1 | 8/2002 | Fraser |
| 6,436,098 B1 | 8/2002 | Michelson |
| 6,436,101 B1 | 8/2002 | Hamada |
| 6,447,512 B1 | 9/2002 | Landry et al. |
| 6,447,544 B1 | 9/2002 | Michelson |
| 6,454,805 B1 | 9/2002 | Baccelli et al. |
| 6,454,806 B1 | 9/2002 | Cohen et al. |
| 6,458,159 B1 | 10/2002 | Thalgott |
| 6,468,311 B2 | 10/2002 | Boyd et al. |
| 6,478,800 B1 | 11/2002 | Fraser et al. |
| 6,478,801 B1 | 11/2002 | Ralph et al. |
| 6,478,823 B1 | 11/2002 | Michelson |
| 6,482,233 B1 | 11/2002 | Aebi et al. |
| 6,488,710 B2 | 12/2002 | Besselink |
| 6,491,724 B1 | 12/2002 | Ferree |
| 6,500,180 B1 | 12/2002 | Foley et al. |
| 6,517,544 B1 | 2/2003 | Michelson |
| 6,527,803 B1 | 3/2003 | Crozet et al. |
| 6,537,279 B1 | 3/2003 | Michelson |
| 6,551,316 B1 | 4/2003 | Rinner et al. |
| 6,562,074 B2 | 5/2003 | Gerbec et al. |
| 6,565,574 B2 | 5/2003 | Michelson |
| 6,569,168 B2 | 5/2003 | Lin |
| 6,582,431 B1 | 6/2003 | Ray |
| 6,585,749 B2 | 7/2003 | Hanson |
| 6,589,247 B2 | 7/2003 | McGahan et al. |
| 6,599,291 B1 | 7/2003 | Foley et al. |
| 6,599,292 B1 | 7/2003 | Ray |
| 6,607,559 B2 | 8/2003 | Ralph et al. |
| 6,635,086 B2 | 10/2003 | Lin |
| 6,641,582 B1 | 11/2003 | Hanson et al. |
| 6,641,614 B1 | 11/2003 | Wagner et al. |
| 6,648,917 B2 | 11/2003 | Gerbec et al. |
| 6,652,533 B2 | 11/2003 | O'Neil |
| 6,666,866 B2 | 12/2003 | Martz et al. |
| 6,676,703 B2 | 1/2004 | Biscup |
| 6,706,070 B1 | 3/2004 | Wagner et al. |
| 6,712,819 B2 | 3/2004 | Zucherman et al. |
| 6,712,825 B2 | 3/2004 | Aebi et al. |
| 6,719,796 B2 | 4/2004 | Cohen et al. |
| 6,730,126 B2 | 5/2004 | Boehm, Jr. et al. |
| 6,740,088 B1 | 5/2004 | Kozak et al. |
| 6,743,255 B2 | 6/2004 | Ferree |
| 6,746,450 B1 | 6/2004 | Wall et al. |
| 6,746,454 B2 | 6/2004 | Winterbottom et al. |
| 6,749,635 B1 | 6/2004 | Bryan |
| 6,755,841 B2 | 6/2004 | Fraser et al. |
| 6,758,849 B1 | 7/2004 | Michelson |
| 6,767,367 B1 | 7/2004 | Michelson |
| 6,770,074 B2 | 8/2004 | Michelson |
| 6,770,096 B2 | 8/2004 | Bolger et al. |
| 6,793,658 B2 | 9/2004 | LeHuec et al. |
| 6,824,565 B2 | 11/2004 | Muhanna et al. |
| 6,827,740 B1 | 12/2004 | Michelson |
| 6,830,589 B2 | 12/2004 | Erickson |
| 6,840,941 B2 | 1/2005 | Rogers et al. |
| 6,852,129 B2 | 2/2005 | Gerbec et al. |
| 6,855,148 B2 | 2/2005 | Foley et al. |
| 6,863,673 B2 | 3/2005 | Gerbec et al. |
| 6,875,213 B2 | 4/2005 | Michelson |
| 6,884,242 B2 | 4/2005 | LeHuec et al. |
| 6,893,464 B2 | 5/2005 | Kiester |
| 6,902,566 B2 | 6/2005 | Zucherman et al. |
| 6,923,830 B2 | 8/2005 | Michelson |
| 6,929,647 B2 | 8/2005 | Cohen |
| 6,955,691 B2 | 10/2005 | Chae et al. |
| 6,966,912 B2 | 11/2005 | Michelson |
| 6,974,480 B2 | 12/2005 | Messerli et al. |
| 6,976,988 B2 | 12/2005 | Ralph et al. |
| 6,981,975 B2 | 1/2006 | Michelson |
| 6,986,772 B2 | 1/2006 | Michelson |
| 7,004,947 B2 | 2/2006 | Shluzas et al. |
| 7,018,415 B1 | 3/2006 | McKay |
| 7,018,416 B2 | 3/2006 | Hanson et al. |
| 7,033,394 B2 | 4/2006 | Michelson |
| 7,041,135 B2 | 5/2006 | Michelson |
| 7,051,417 B2 | 5/2006 | Michelson |
| 7,060,073 B2 | 6/2006 | Frey |
| 7,066,961 B2 | 6/2006 | Michelson |
| 7,070,598 B2 | 7/2006 | Lim et al. |
| 7,077,864 B2 | 7/2006 | Byrd, III et al. |
| 7,081,118 B2 | 7/2006 | Weber |
| 7,083,650 B2 | 8/2006 | Moskowitz et al. |
| 7,087,055 B2 | 8/2006 | Lim et al. |
| 7,094,257 B2 | 8/2006 | Mujwid et al. |
| 7,108,698 B2 | 9/2006 | Robbins |
| 7,112,206 B2 | 9/2006 | Michelson |
| 7,112,224 B2 | 9/2006 | Liu |
| 7,115,132 B2 | 10/2006 | Errico |
| 7,115,143 B1 | 10/2006 | Michelson |
| 7,118,579 B2 | 10/2006 | Michelson |
| 7,135,043 B2 | 11/2006 | Nakahara et al. |
| 7,137,997 B2 | 11/2006 | Paul |
| 7,144,275 B2 | 12/2006 | Iida |
| 7,153,303 B2 | 12/2006 | Squires |
| 7,153,304 B2 | 12/2006 | Robie et al. |
| 7,160,304 B2 | 1/2007 | Michelson |
| 7,163,561 B2 | 1/2007 | Michelson |
| 7,166,129 B2 | 1/2007 | Michelson |

| | | |
|---|---|---|
| 7,166,130 B2 | 1/2007 | Ferree |
| 7,169,152 B2 | 1/2007 | Foley |
| 7,169,153 B2 | 1/2007 | Keller |
| 7,169,182 B2 | 1/2007 | Errico et al. |
| 7,172,627 B2 | 2/2007 | Fiere et al. |
| 7,189,242 B2 | 3/2007 | Boyd et al. |
| 7,189,244 B2 | 3/2007 | Newton et al. |
| 7,207,991 B2 | 4/2007 | Michelson |
| 7,211,085 B2 | 5/2007 | Michelson |
| 7,211,100 B2 | 5/2007 | Hanson |
| 7,217,292 B2 | 5/2007 | Ralph et al. |
| 7,217,293 B2 | 5/2007 | Branch, Jr. |
| 7,229,477 B2 | 6/2007 | Biscup |
| 7,232,463 B2 | 6/2007 | Falahee |
| 7,235,081 B2 | 6/2007 | Errico et al. |
| 7,235,082 B2 | 6/2007 | Bartish |
| 7,244,275 B2 | 7/2007 | Michelson |
| 7,255,698 B2 | 8/2007 | Michelson |
| 7,288,093 B2 | 10/2007 | Michelson |
| 7,288,095 B2 | 10/2007 | Baynham et al. |
| 7,303,565 B2 | 12/2007 | Buttermann |
| 7,594,932 B2 | 9/2009 | Aferzon et al. |
| 7,727,280 B2 | 6/2010 | McLuen |
| 7,749,274 B2 | 7/2010 | Razian |
| 8,100,972 B1 | 1/2012 | Bruffey et al. |
| 8,142,508 B1 | 3/2012 | Bruffey et al. |
| 8,167,950 B2 * | 5/2012 | Aferzon et al. ............ 623/17.16 |
| 2002/0128713 A1 | 9/2002 | Ferree |
| 2003/0023312 A1 | 1/2003 | Thalgott |
| 2003/0040798 A1 | 2/2003 | Michelson |
| 2004/0117020 A1 | 6/2004 | Frey et al. |
| 2004/0153156 A1 | 8/2004 | Cohen |
| 2004/0215198 A1 | 10/2004 | Marnay |
| 2005/0021041 A1 | 1/2005 | Michelson |
| 2005/0080422 A1 | 4/2005 | Otte |
| 2005/0087628 A1 | 4/2005 | Sayar |
| 2005/0107878 A1 | 5/2005 | Conchy |
| 2005/0187628 A1 | 8/2005 | Michelson |
| 2005/0216083 A1 | 9/2005 | Michelson |
| 2006/0036247 A1 | 2/2006 | Michelson |
| 2006/0058793 A1 | 3/2006 | Michelson |
| 2006/0058876 A1 | 3/2006 | McKinley |
| 2006/0058878 A1 | 3/2006 | Michelson |
| 2006/0069442 A1 | 3/2006 | Michelson |
| 2006/0079962 A1 | 4/2006 | Michelson |
| 2006/0085001 A1 | 4/2006 | Michelson |
| 2006/0100633 A1 | 5/2006 | Michelson |
| 2006/0106395 A1 | 5/2006 | Link |
| 2006/0116768 A1 | 6/2006 | Krueger et al. |
| 2006/0122701 A1 | 6/2006 | Kiester |
| 2006/0142859 A1 | 6/2006 | McLuen |
| 2006/0200138 A1 | 9/2006 | Michelson |
| 2006/0200164 A1 | 9/2006 | Michelson |
| 2006/0206207 A1 | 9/2006 | Dryer et al. |
| 2006/0241764 A1 | 10/2006 | Michelson |
| 2006/0265077 A1 | 11/2006 | Zwirkoski |
| 2007/0032871 A1 | 2/2007 | Michelson |
| 2007/0055376 A1 | 3/2007 | Michelson |
| 2007/0100452 A1 | 5/2007 | Prosser |
| 2007/0276370 A1 | 11/2007 | Altarac |
| 2007/0288007 A1 | 12/2007 | Burkus et al. |
| 2007/0293949 A1 | 12/2007 | Salerni |
| 2008/0027550 A1 | 1/2008 | Link et al. |
| 2008/0103501 A1 | 5/2008 | Ralph et al. |
| 2008/0132949 A1 | 6/2008 | Aferzon et al. |
| 2009/0265007 A1 | 10/2009 | Colleran |
| 2010/0030334 A1 | 2/2010 | Molz, IV |
| 2010/0305704 A1 | 12/2010 | Messerli et al. |

FOREIGN PATENT DOCUMENTS

| | | |
|---|---|---|
| EP | 1338257 | 8/2003 |
| EP | 1374809 | 1/2004 |
| FR | 2880795 | 1/2005 |
| JP | 2010051651 | 3/2010 |
| WO | WO-2010037926 | 4/2010 |

* cited by examiner

VERTEBRAL INTERBODY COMPRESSION IMPLANT

CROSS-REFERENCE TO RELATED APPLICATIONS

This application relates to, and claims the benefit of the filing date of U.S. provisional patent application Ser. No. 60/987,111 entitled VERTEBRAL INTERBODY COMPRESSION IMPLANT, filed Nov. 12, 2007, the entire contents of which are incorporated herein by reference for all purposes.

BACKGROUND INFORMATION

The invention relates in general to skeletal stabilization systems, and in particular to implants, surgical guides, delivery instruments and methods for delivering and attaching implants to bony structures such as a vertebrae.

The human spine is a complex structure designed to achieve a myriad of tasks, many of them of a complex kinematic nature. The spinal vertebrae allow the spine to flex in three axes of movement relative to the portion of the spine in motion. These axes include the horizontal (i.e., bending either forward/anterior or aft/posterior), roll (i.e., lateral bending to either left or right side), and rotation (i.e., twisting of the shoulders relative to the pelvis).

The intervertebral spacing (e.g., between neighboring vertebrae) in a healthy spine is maintained by a compressible and somewhat elastic disc. The disc serves to enable the spine to move about the various axes of rotation and through the various arcs and movements required for normal mobility. The elasticity of the disc maintains the spacing between the vertebrae during flexion and lateral bending of the spine, allowing room or clearance for compression of neighboring vertebrae. In addition, the disc enables relative rotation about the vertical axis of neighboring vertebrae, allowing for the twisting of the shoulders relative to the hips and pelvis. The clearance between neighboring vertebrae, as maintained by a healthy disc, is also important to allow the nerves from the spinal cord to extend out from the spine, e.g., between neighboring vertebrae, without being squeezed or impinged by the adjacent vertebrae.

In situations (e.g., based upon injury or otherwise) where a disc is not functioning properly, the inter-vertebral disc tends to compress, and in doing so pressure is exerted on nerves extending from the spinal cord by the reduced inter-vertebral spacing. Various other types of nerve problems may be experienced in the spine, such as exiting nerve root compression in neural foramen, passing nerve root compression, and enervated annulus (i.e., where nerves grow into a cracked/compromised annulus, causing pain every time the disc/annulus is compressed), as examples. Many medical procedures have been devised to alleviate such nerve compression and the pain that results from the nerve pressure. Many of these procedures revolve around attempts to prevent the vertebrae from moving too close to each other by surgically removing an improperly functioning disc and replacing it with a lumbar interbody fusion device or spacer. Although prior interbody devices, including spacers, may be effective at improving the condition of a patient, the vertebrae of the spine, body organs, the spinal cord, other nerves, and other adjacent bodily structures make it difficult to obtain surgical access to the locations between the vertebrae where the spacer is to be installed.

PLIF is an acronym for Posterior Lumbar Interbody Fusion. PLIF is a surgical procedure that may be used to treat the conditions mentioned above. In this procedure, a spacer or implant, bone graft, or a bone graft substitute, may be placed between vertebrae to fuse them and create more stable spine. The bone graft is inserted into the disc space from the back (posterior). In addition, spinal instrumentation such as screws and rods may be used to hold the spine in position and help promote successful fusion. ALIF stands for Anterior Lumbar Interbody Fusion. ALIF is a surgical procedure similar to PLIF, but it is done from the front (anterior) of the body, usually through an incision in the lower abdominal area or on the side. The incision may involve cutting through, and later repairing, the muscles in the lower abdomen. In recent years, surgeons have begun to use a TLIF procedure (Transforaminal Lumbar Interbody Fusion). A TLIF may accomplish the same goals as a PLIF procedure, however in the TLIF technique the bone graft or implant in inserted into the disc space laterally or from the side. The TLIF technique usually results in the nerve roots being moved less during the procedure, as compared to a PLIF, and may reduce the risk of scarring or damaging the nerve roots. XLIF stands for extreme Lateral Interbody Fusion. XLIF is also a relatively new surgical procedure and avoids an incision that traverses the abdomen and also avoids cutting or disrupting the muscles of the back. In surgical procedure, the disk space is accessed from a very small incision on the patient's side. The bone graft or implant may then be inserted into the disc space laterally or from the side.

SUMMARY

An implant for securing boney structures is provided, comprising an engagement mechanism having bone engagement members slideably and rotatably coupled to a moveable housing in the implant, where the bone engagement members rotate away from the implant when the housing is moved by a force transfer mechanism.

BRIEF DESCRIPTION OF THE DRAWINGS

For a more complete understanding of the present invention and the advantages thereof, reference is now made to the following Detailed Description taken in conjunction with the accompanying drawings, in which.

It should be noted the drawings are not intended to represent the only aspect of the invention. Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, and composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the invention is intended to encompass within its scope such processes, machines, manufacture, compositions of matter, means, methods, or steps.

DETAILED DESCRIPTION

Specific examples of components, methods, and arrangements are described below to simplify the present disclosure. These are, of course, merely examples and are not intended to limit the invention from that described in the claims. Well-known elements are presented without detailed description in order not to obscure the present invention in unnecessary detail. For the most part, details unnecessary to obtain a complete understanding of the present invention have been omitted inasmuch as such details are within the skills of persons of ordinary skill in the relevant art.

Figure 1:
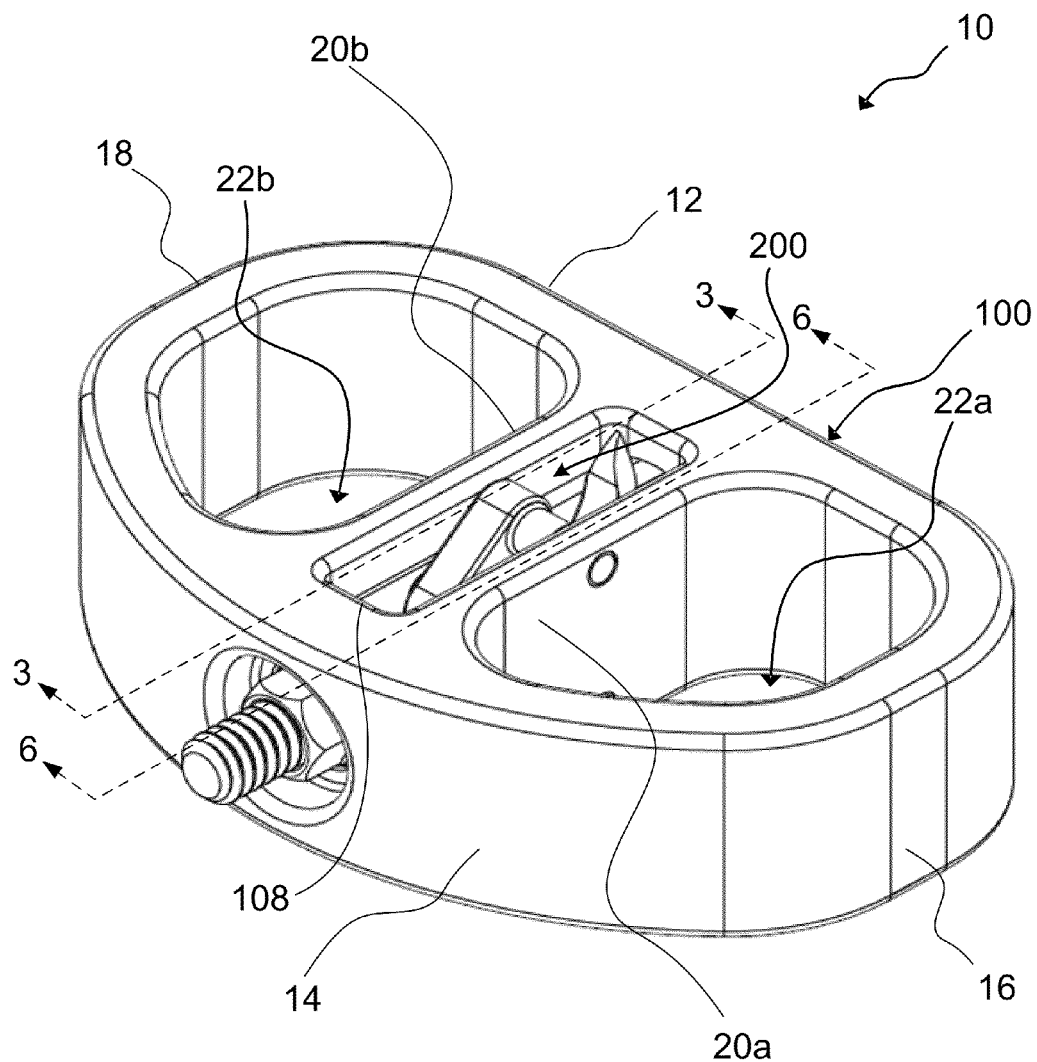
FIG. 1 is a perspective view of one possible embodiment of a vertebral interbody compression implant.

Turning now to FIG. 1, there is presented a front perspective view of one possible embodiment of a perspective view of a vertebral interbody compression implant 10. The implant 10 may incorporate a main body 100 and a compression mechanism 200. The implant 10 may be inserted between two adjacent bony structures (for example two adjacent vertebrae of the spine) using various instruments to stabilize or fuse the adjacent bony structures. The compression mechanism 200 may aid in securing the implant 10 to the adjacent boney structures and may act to compress the adjacent boney structures against the implant 10 which may promote bone fusion. The implant 10 may be used alone or in conjunction with other implants to stabilize or fuse different bony structures. Accordingly, the main body 100 and the compression mechanism 200 may interrelate to securely attach and engage the implant 10 to two adjacent vertebral end plates a spine to provide for adequate stabilization or fusion.

In certain embodiments, the main body 100 may have a leading end 14 and a trailing end 12 opposite the leading end 14. The leading end 14 and the trailing end 12 may be connected by a pair of opposite sides 16 and 18. The leading end 14 and trailing end 12 may have a length and a height and the pair of opposite sides 16 and 18 may have a height and a width. In certain embodiments, the length of the leading end 14 and the trailing end 12 may be greater than the width of the opposite sides 16 and 8. The main body 100 may have one or more reinforcing walls 20a and 20b connecting the leading end 14 and the trailing end 12 which may be located between the pair of opposite sides 16 and 18. The reinforcing walls 20a and 20b may run generally through the center of the body between the pair of opposite sides 16 and 18. The main body 100 may have one or more openings 22a and 22b located between the opposite sides, between the lead and trailing ends 14 and 12 and bounded by the reinforcing walls 20a and 20b. The openings 22a and 22b may be filled with bone growth material such as BMP (bone morphogenetic protein), autograft, allograft, ceramics or other biocompatible material that aids in bone fusion. The leading end 14, the trailing end 12 and the reinforcing walls 20a and 20b may define a slot 108 of the implant 10. that extends through the main body 100. The slot 108 may at least partially enclose the compression mechanism 200. The leading end 14, the trailing end 12, the opposite sides 16 and 18 may have a contoured upper surface and a contoured lower surface that conforms to the shape of a vertebral endplate. The upper surface and the lower surfaces may have projections, such as teeth, which may aid in gripping the vertebral end plate surface.

Figure 2:
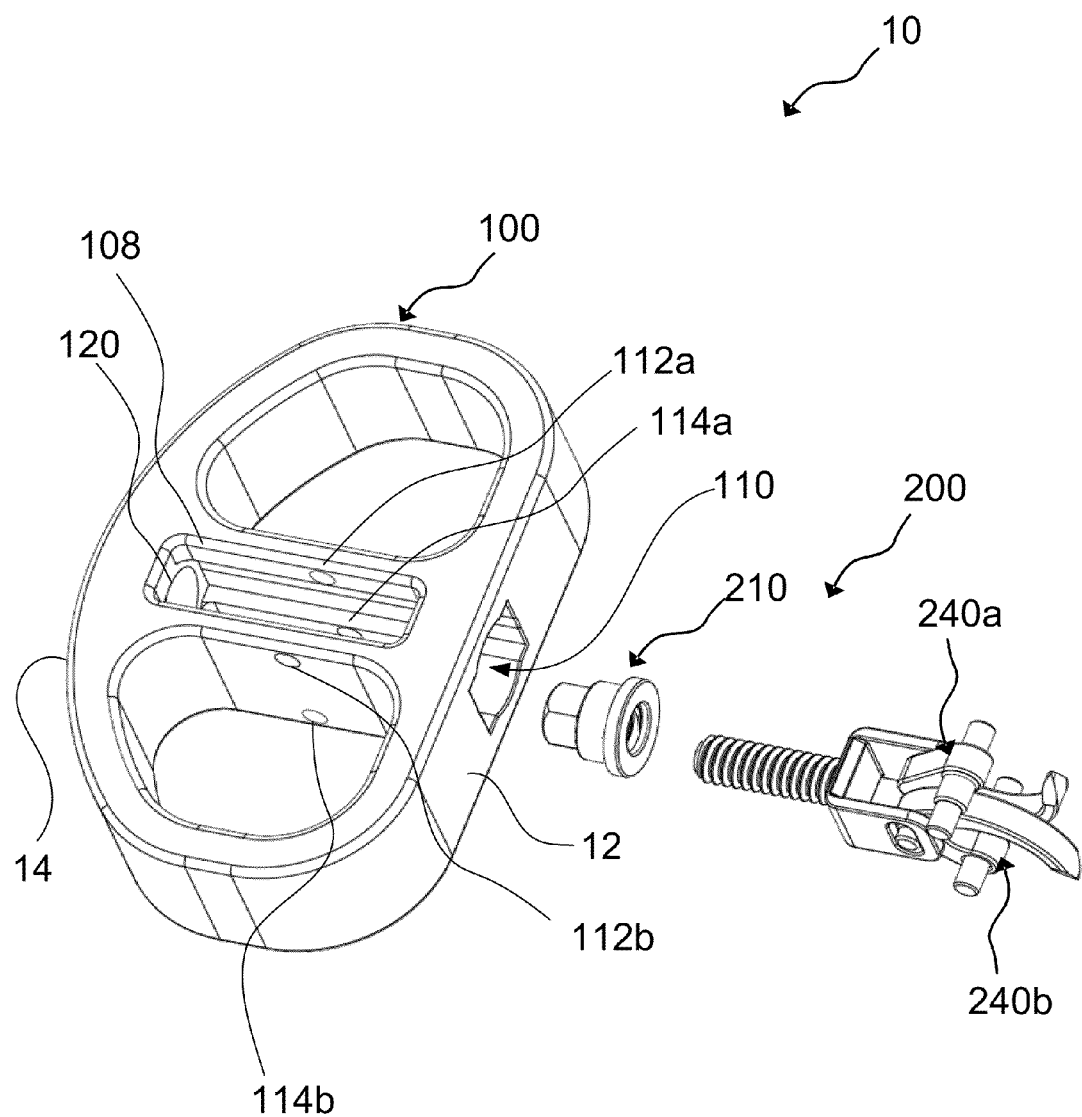
FIG. 2 is an exploded assembly view of one embodiment the vertebral interbody compression implant of FIG. 1.

Referring to FIG. 2, there is presented an exploded assembly view of one embodiment the implant 10 illustrating the main body 100 and the compression mechanism 200. The reinforcing walls 20a and 20b may each have an upper aperture 112a and 112b and a lower apertures 114a and 114b extending generally transversely into the reinforcing walls 20a and 20b. The upper apertures 112a and 112b and the lower apertures 114a and 114b may aid in coupling the compression mechanism 200 to the main body 100. The main body 100 may have an inner surface defining a generally rectangular shaped passage 110 that is dimensioned to slidingly receive the compression mechanism 100. The passage 110 may extend from the trailing end 14 toward the leading end along a longitudinal axis of the main body 100. One or more sides of the passage 110 may be enlarged, which may allow the main body 100 to receive the compression mechanism 200.

As will be explained in greater detail later, the compression mechanism 200 may include a pair of bone engagement members 240a and 240b and a drive element 210. In certain embodiments there may be a plurality of bone engagement members 240a and 240b which may be arranged in an anterior-posterior direction or a medial-lateral direction with respect to a pair of vertebral end plates. The drive element 210 may be dimensioned to pass through the passage 110. The leading end 14 of the main body 100 may have a first inner surface 120 adjacent to the passage 110 that defines a bore that is dimensioned to receive at least a portion of the drive element 210 and a portion of the compression mechanism 200 (as well be described in greater detail in FIGS. 6, 7A, 7B). The pair of bone engagement members 240a and 240b may be dimensioned to at least partially pass through the slot 108 of the main body 100.

Figure 3:
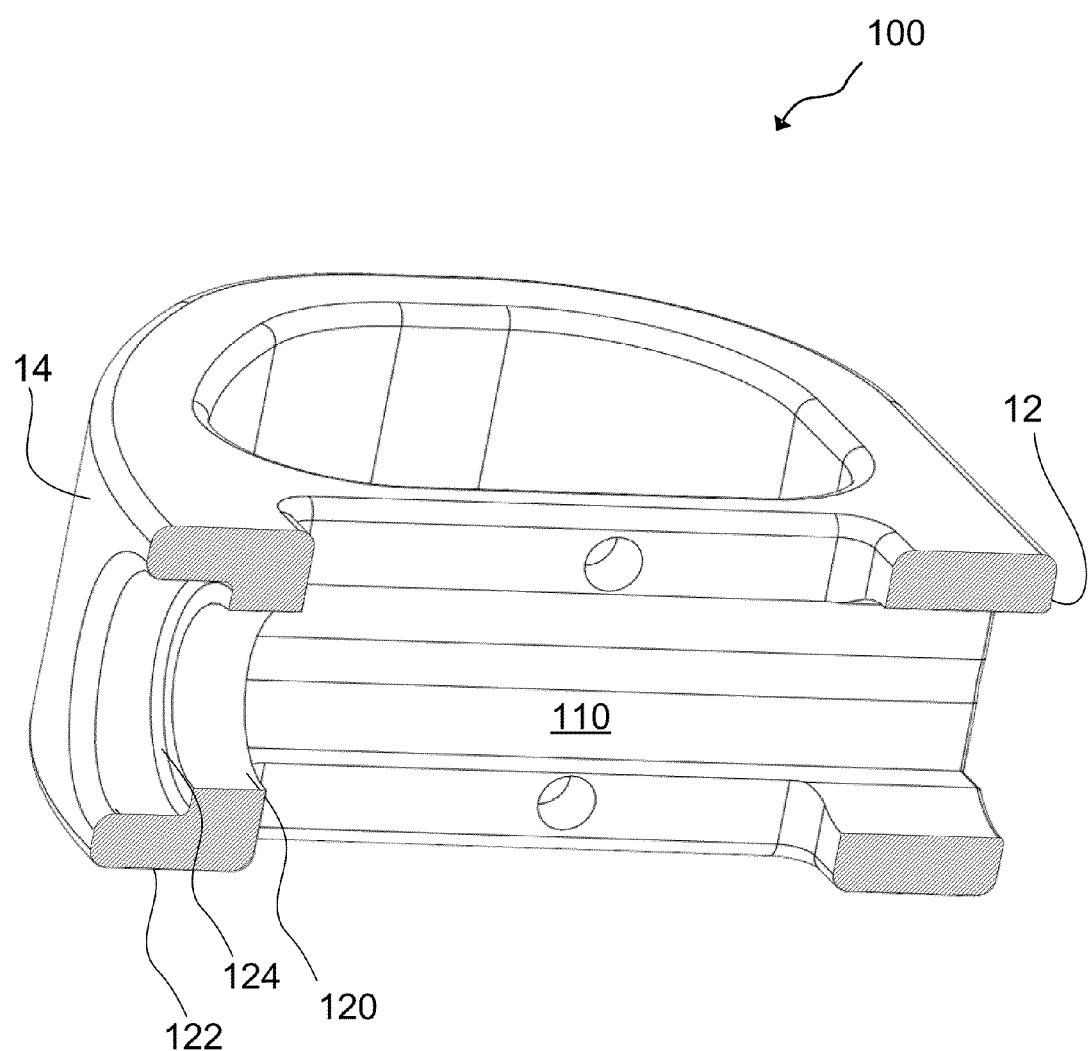
FIG. 3 is a perspective cross section view of one possible embodiment of a main body which may be incorporated in the vertebral interbody compression implant of FIG. 1.

Referring now to FIG. 3, there is shown is a perspective cross sectional view of the main body 100 taken along a longitudinal axis (line 3-3 shown in FIG. 1) between the leading end 14 and the trailing end 12. The main body 100 may have a second inner surface 122 adjacent to and coaxial with the first inner surface that defines a recess that extends into the leading end 14. In certain embodiments, the diameter of the first inner surface 120 may be less than a diameter of the second inner surface 122. The second inner surface 122 may be dimensioned to receive at least a portion of the drive element 210 and a portion of the coupling mechanism 200. A shoulder 124 may be located between the first inner surface 120 and the second inner surface 122.

Figure 4:
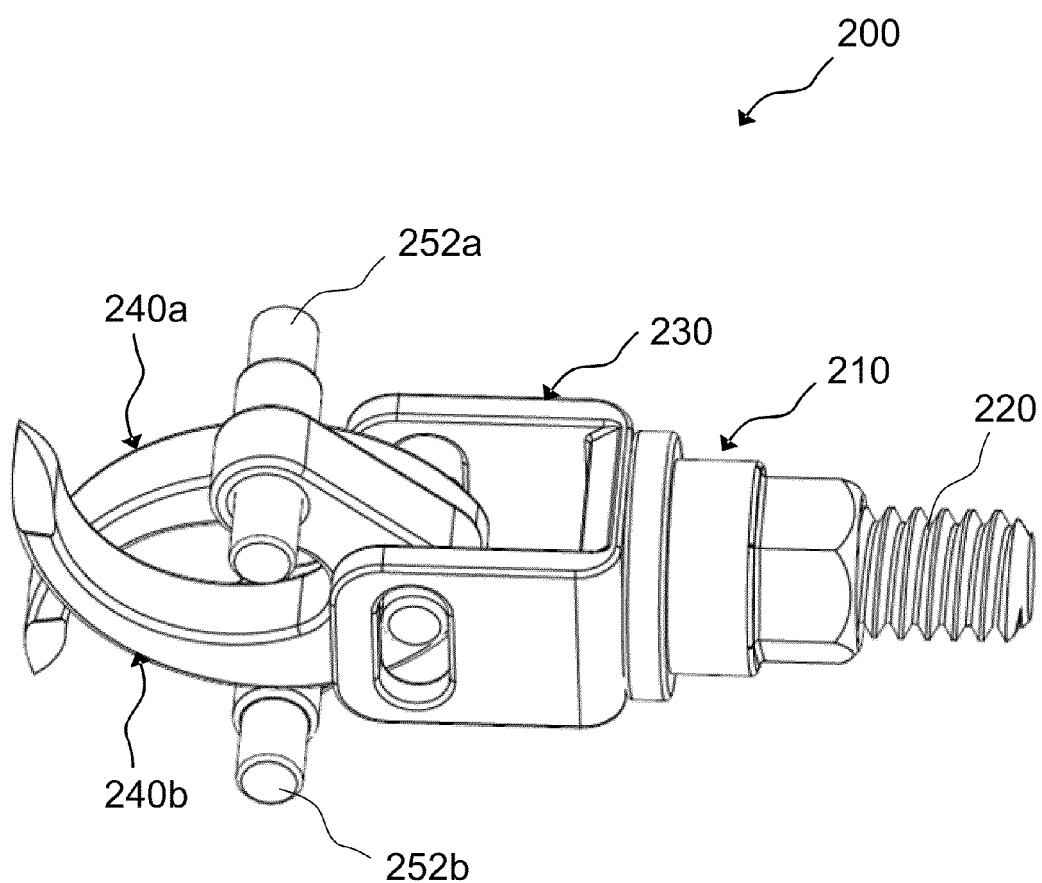
FIG. 4 is a perspective view of one possible embodiment a compression mechanism which may be incorporated in the vertebral interbody compression implant of FIG. 1.

Referring to FIG. 4, there is shown a perspective view of the compression mechanism 200. In certain embodiments the compression mechanism 200 may incorporate the pair of bone engagement members 240a and 240b, a first and second coupling members 252a and 252b, a housing 230, the drive element 210 and a drive shaft 220. As will be explained in greater detail below, the drive element 210 and the drive shaft 220 may apply a force to the housing 230 to move the bone engagement members 240a and 240b. The compression mechanism 200 may have a first position and a second position. The second position may allow the bone engagement members 240a and 240b to secure and/or compress a pair of adjacent boney structures (not shown).

Figure 5:
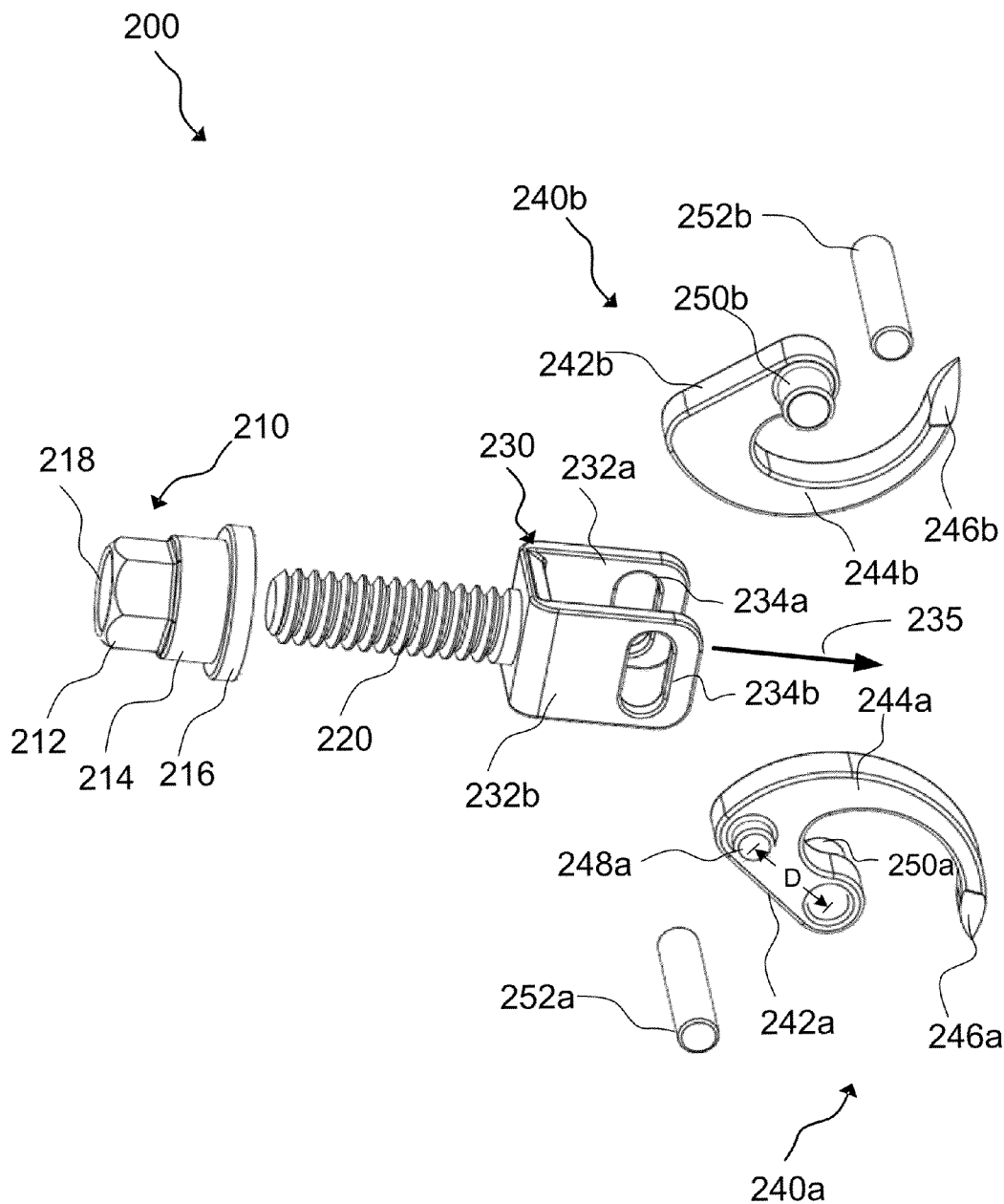
FIG. 5 is an exploded view of one possible embodiment of the compression mechanism of FIG. 4.

Referring to FIG. 5, there is shown an exploded assembly view of the compression mechanism 200 illustrating the pair of bone engagement members 240a and 240b, a first and second coupling members 252a and 252b, the housing 230, the drive element 210 and the drive shaft 220. The drive element 210 may have an inner surface 218 that defines an opening there through. The inner surface 218 may be partially threaded (not shown) and dimensioned to receive the drive shaft 220.

The drive element 210 may incorporate a force transfer member 212, a centering element 214 and a shoulder 216. The force transfer member 212 may have an outer surface that may be utilized as a driving means to translate the force transfer member 212 in relation to the drive shaft 220. A surgeon may apply a linear or non linear force (for example torque) to the force transfer member 212. The outer surface of the force transfer member 212 may have various geometries such as torx, hex, stars, oblong, rectangular and square shapes which may allow for the transfer of a linear or non linear force. In alternative embodiments the inner surface of the force transfer member may have various geometries such as torx, hex, stars, oblong, rectangular and square shapes which may allow for the transfer of a linear or non linear force. The centering element 214 may be generally cylindrical in shape which may aid in the alignment of the compression mechanism relative to the implant 100. As will be described in greater detail below, the shoulder 216 may be generally circular in shape and may aid in securing the compression mechanism 200 to the implant 100.

The drive element 210 may couple to the drive shaft 220. The drive shaft 220 may be generally cylindrical in shape and may extend along a longitudinal axis. The drive shaft 220 may have a threaded outer surface that engages the threaded inner surface of the drive element 210. One end of the drive shaft 220 may couple to the housing 230. The drive shaft 220 and the housing 230 may be an integral component or a two piece design assembled using conventional assembly methods such as welding, pinning, adhesives, press fits or other means known to those skilled in the art. The housing 230 may extend along a longitudinal axis 235 and may have a first end and a second end. The housing 230 may have a generally rectangular or cylindrical shape. In certain embodiments, the housing 230 may have a pair of arms 232a and 232b located between the first end and the second end that extend out in a first direction and define an open channel there between. Each arm 232a and may have a slot 234a and 234b that extends in a generally transverse direction to the longitudinal axis 235 of the housing 230.

The bone engagement members 240a and 240b may be dimensioned to be received within the channel of the housing 230. In certain embodiments the bone engagement members 240a and 240b may have a first arm 242a and 242b that extend along a first axis and a second arm 244a and 244b that extend along a second arcuate axis, respectively. The first arms 242a and 242b may each have a first end and a second end. The first end of the first arms 242a and 242b may have tab portions, such as first boss 248a and 248b (not shown) and the second end of the first arms 242a and 242b may have second boss 250a and 250b, respectively. The first boss 248a and 248b and the second boss 250a and 250b may extend in a generally transverse direction to the first axis. The first boss 248a and 248b may be dimensioned to be received within the slots 234a and 234b of the first and second arms 232a and 232b, respectively. In certain embodiments, the second boss 250a and 250b may extend in a generally opposite direction to the first boss 248a and 248b, and may have an inner surface defining a bore there through that is dimensioned to receive the first and second coupling members 252a and 252b (as shown in FIG. 4). The distance D (shown in FIG. 5) between the first boss 248a and 248b and the second boss 250a and 250b may provide for a moment arm about which the first arms 242a and 242b may rotate.

The second arms 244a and 244b may have a first end and a second end. The first end of the second arms 244a and 244b may couple to the first end of the first arms 248a and 248b, respectively. The second end of the second arms 244a and 244b may have one or more bone penetrating elements 246a and 246b, such as a spike or a trocar shaped end.

Figure 6:
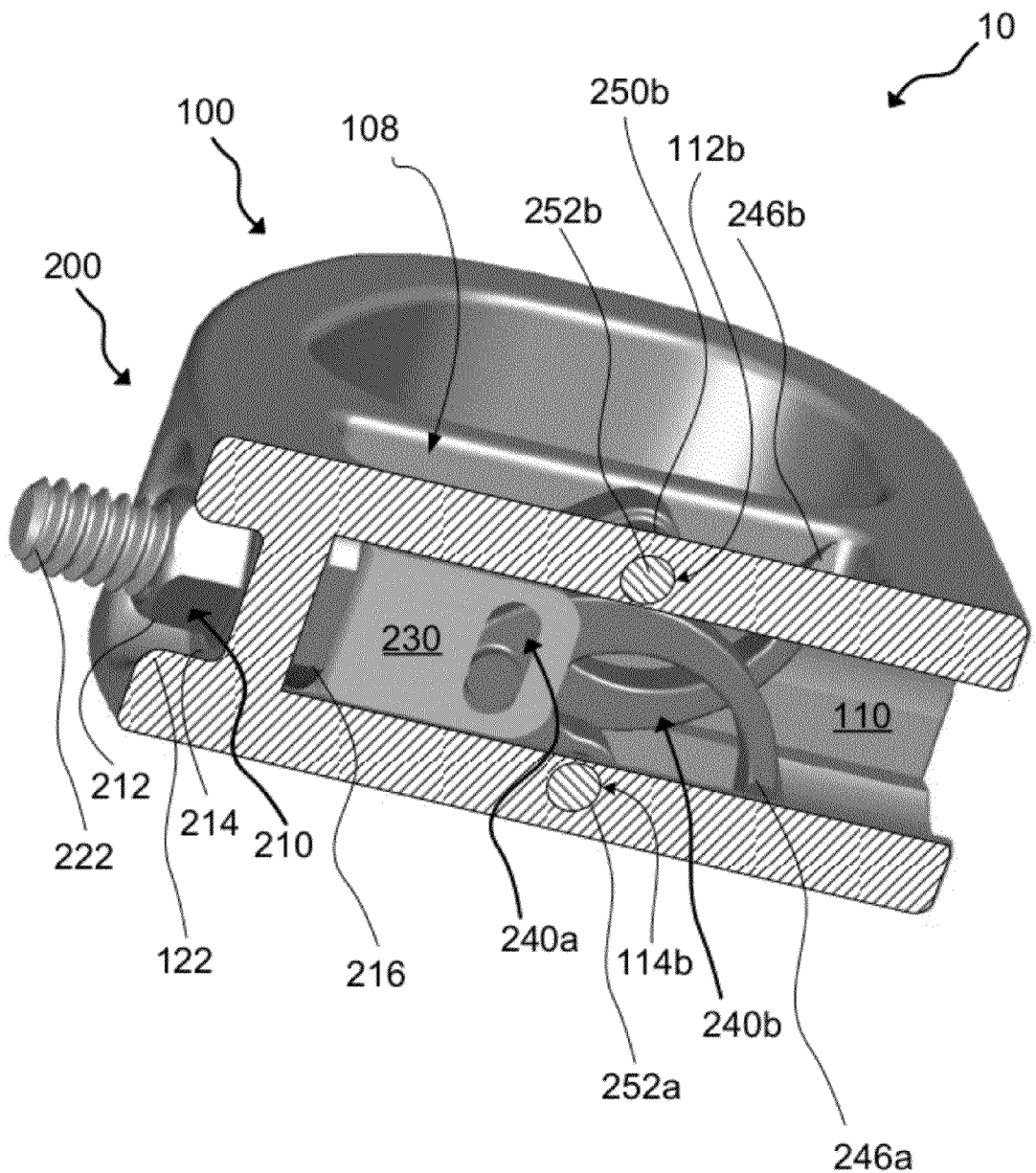
FIG. 6 is a cross section view of the vertebral interbody compression implant of FIG. 1 in a first position.

Turning now to FIG. 6, there is shown a perspective cross sectional view taken along line 6-6 shown in FIG. 1 of the implant 10 illustrating the main body 100 coupled to the compression mechanism 200. The housing 230, the bone engagement members 240a and 240b, the drive shaft 220 and the shoulder 216 of the drive element 210 may slide into and fit within the passage 110. The shoulder 216 may act as a stop to prevent the compression mechanism from advancing too far into the bore 120. The centering element 214 may fit within the bore 120 (not shown) and the force transfer member 212 may fit within the recess 122 of the main body 100. The second boss 250a (not shown) may be aligned with lower apertures 114a and 114b. The coupling element 252a may pass through the lower apertures 114a and 114b and the bore of the second boss 250a to couple the bone engagement member 240b to the main body 100. The second boss 250b may be aligned with upper apertures 112a and 112b. The coupling element 252b may pass through the upper apertures 112a and 112b and the bore of the second boss 250b to couple the bone engagement member 240a to the main body 100. The compression mechanism 200 is shown in the first position in FIG. 6. In the first position the housing 230 may be located adjacent to the force transfer element 210 and the bone penetrating elements 246a and 246b may be located within the slot 108 of the main body 100 or slightly protruding.

Figure 7A:
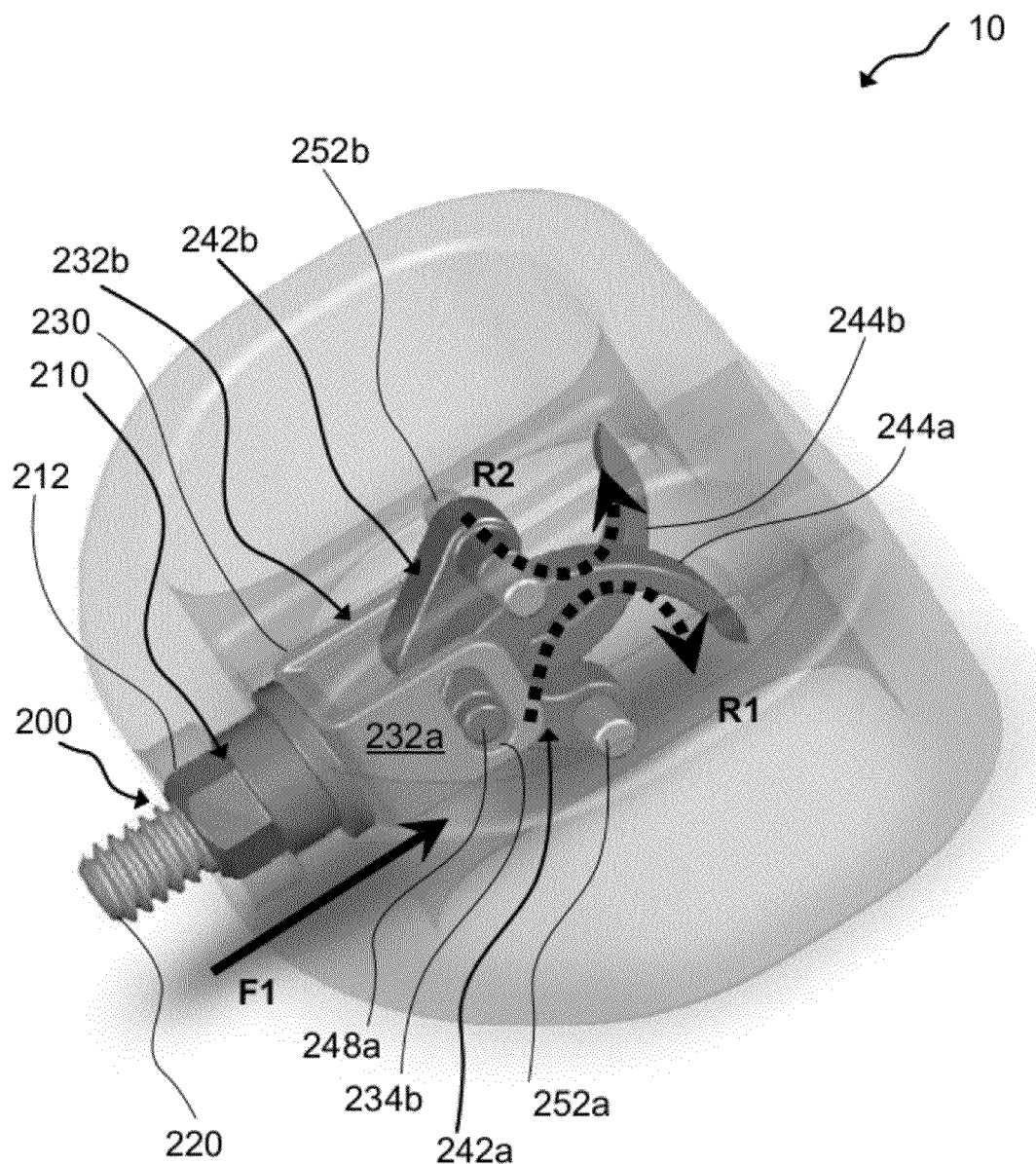
FIG. 7A is a perspective view of the vertebral interbody compression implant of FIG. 1 in a first position.
Figure 7B:
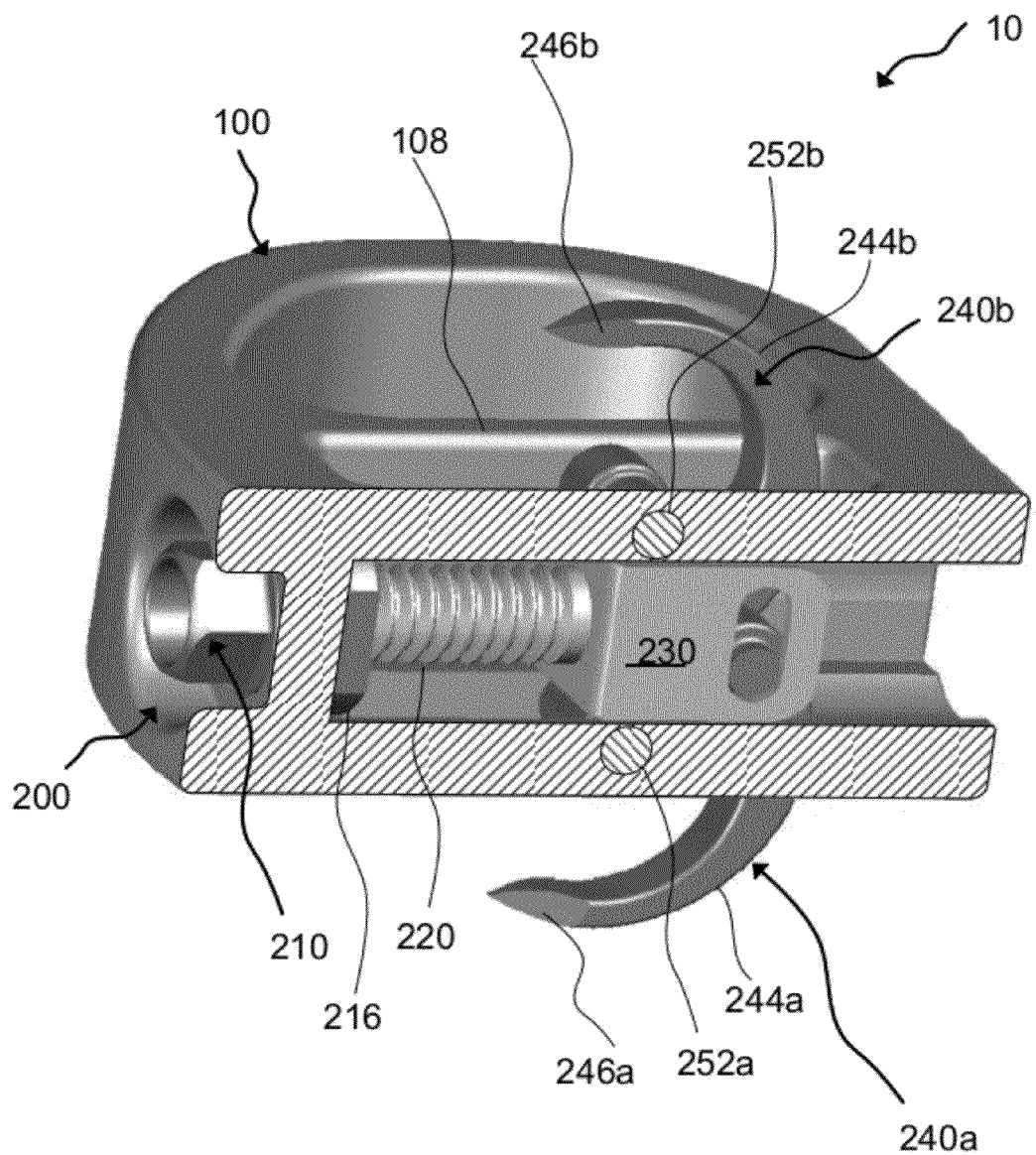
FIG. 7B is a cross section view of the vertebral interbody compression implant of FIG. 1 in a second position.

The compression mechanism 200 may move from the first position to the second position as illustrated in FIGS. 7A and 7B. The main body 100 in FIG. 7A is shown as transparent or removed for clarity purposes. The force transfer mechanism 212 may be moved by a surgeon such that the drive shaft 220 and the attached housing 230 travels axially in relation to the drive element 210, as represented by arrow F1. As the housing 230 travels axially, the arms 232a and 232b of the housing 230 may apply a force on the first boss 248a and 248b of the first end of the first arms 242a and 242b, respectively, causing the first arms 242a and 242b to pivot about the coupling members 252a and 252b. As the first arms 242a and 242b pivot, the first boss 248a and 248b (not shown) may travel axially within the slot 234a (not shown) and 234b of the housing 230. In certain embodiments, the outer surfaces may make contact with the inner surfaces of the slots 234a and 234b to move the first boss 248a and 248b along the slot 234a and 234b. The distance D between the first boss 248a and 248b and the second boss 250a and 250b may provide a moment arm whereby a force applied at the first boss 248a and 248b may cause a torque to be applied to the bone engagement members 240a and 240b. The bone engagement members 240a and 240b may move both with the housing 230 along the longitudinal axis 235, and the bone engagement members 240a and 240b may rotate relative to the housing 230 and the implant 10 about the coupling of the bone engagement members 240a and 240b to the housing 230 at the second boss 250a and 250b. The second arms 244a and 244b may travel along a curved path, as represented by dotted arrows R1 and R2.

As shown in FIG. 7B, the second arms 244a and 244b continue to rotate and protrude out of the slot 108 of the main body 100. FIG. 6C illustrates the implant 10 illustrating the compression mechanism 200 in the second position. In the second position, the housing 230 may be located distal of the force transfer member 210 and the bone engagement members 240a and 240b may protrude out of the slot 108 of the implant 100. The bone penetrating elements 246a and 246b may engage one or more adjacent bony structures, for example a pair of vertebrae (not shown). The second arms 244a and 244b may continue to rotate into the adjacent vertebrae which may pull or compress the vertebrae against the implant 10.

It should be noted that other means and mechanisms may be used to deploy the bone engagement anchors from the first position to the second position. The drive element 210 and the drive shaft 220 are only one example of such a means. Other mechanisms may include cams, linkages and wedges which may apply a force on the bone engagement anchors and cause them to at least partially rotate out of the slot 108 and into the adjacent boney structure.

Figure 8:
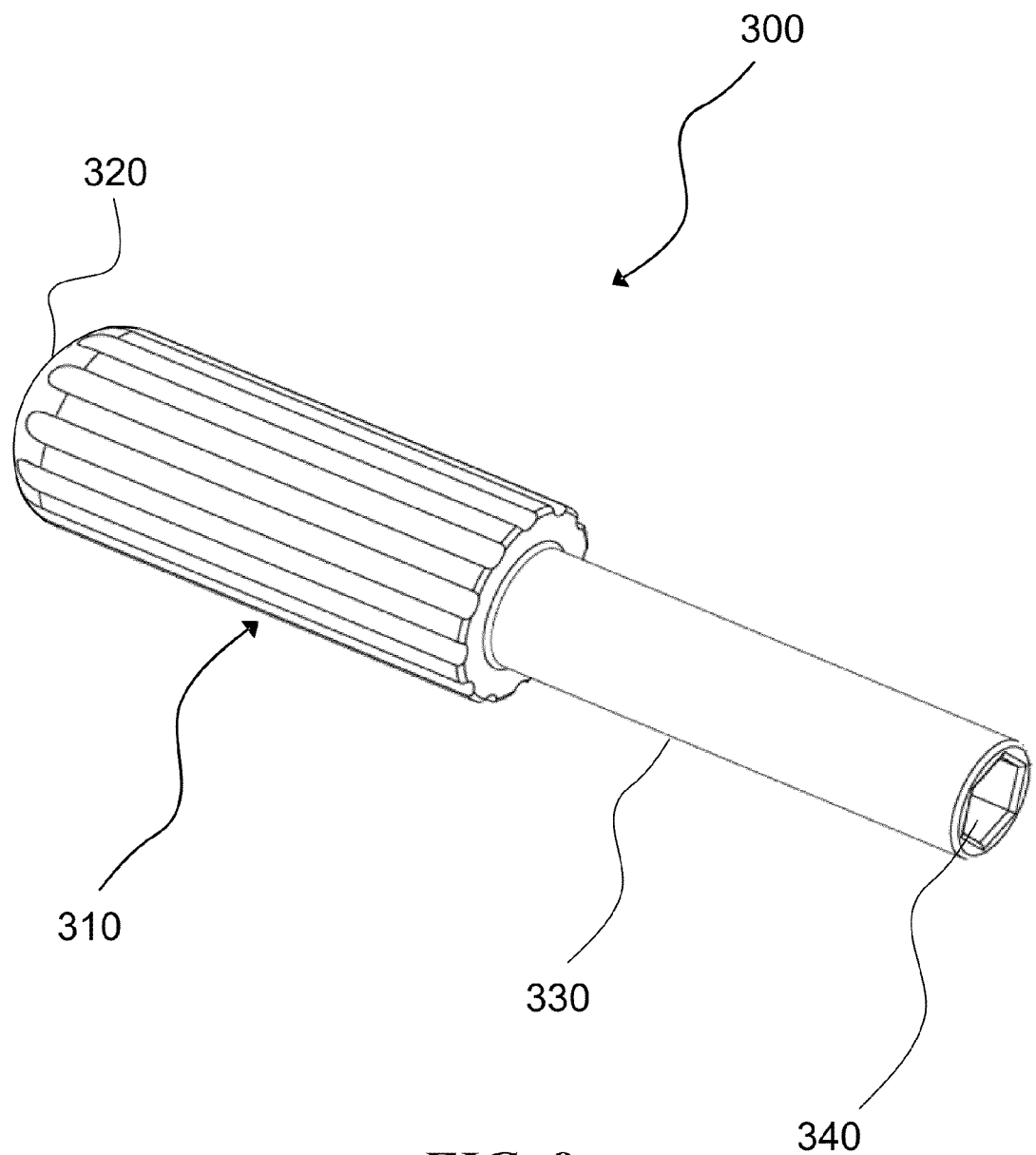
FIG. 8 is a perspective view of one possible embodiment of an insertion instrument which may be used to implant the vertebral interbody compression implant of FIG. 1.

Turning to FIG. 8, there is shown one possible embodiment of an implant inserter 300 which may be used to insert the implant 10 shown in FIGS. 7A and 7B. The implant inserter 300 may have a first end and a second end. The first end of the implant inserter 300 may have a handle 310. The proximal end of the handle 310 may have an impaction surface 320. The impaction surface 320 may have a curved or dome-shaped geometry to receive an impact force from another instrument, such as a mallet. The distal end of the handle 310 may couple to a shaft 330. The handle 310 and the shaft 330 may be permanently attached or may be temporarily attached with a quick release mechanism. The distal end of the shaft 330 may have an outer surface that is dimensioned to fit within the second inner surface 122 of the main body 100. The distal end of the shaft 330 may have an inner surface 340 that is dimensioned to couple and apply a linear or non linear force to the driver element 210 (not shown). The geometry of the inner surface 340 may correspond to the geometry of the outer surface of the force transfer member 212, as shown in FIG. 7A. The inner surface 340 may have various geometries such as torx, hex, stars, oblong, rectangular and square shapes which may allow for the transfer of a linear or non linear force. In alternative embodiments the outer surface of the distal end of the shaft 330 may have various geometries such as torx, hex, stars, oblong, rectangular and square shapes which may allow for the transfer of a linear or non linear force to the implant 10. The inner surface 340 may engage the force transfer member 212 to deploy the bone engagement members 240a and 240b, as shown in FIG. 7A. In some embodiment, the handle 310 may be actuated to rotate the implant inserter 300.

Figure 9:
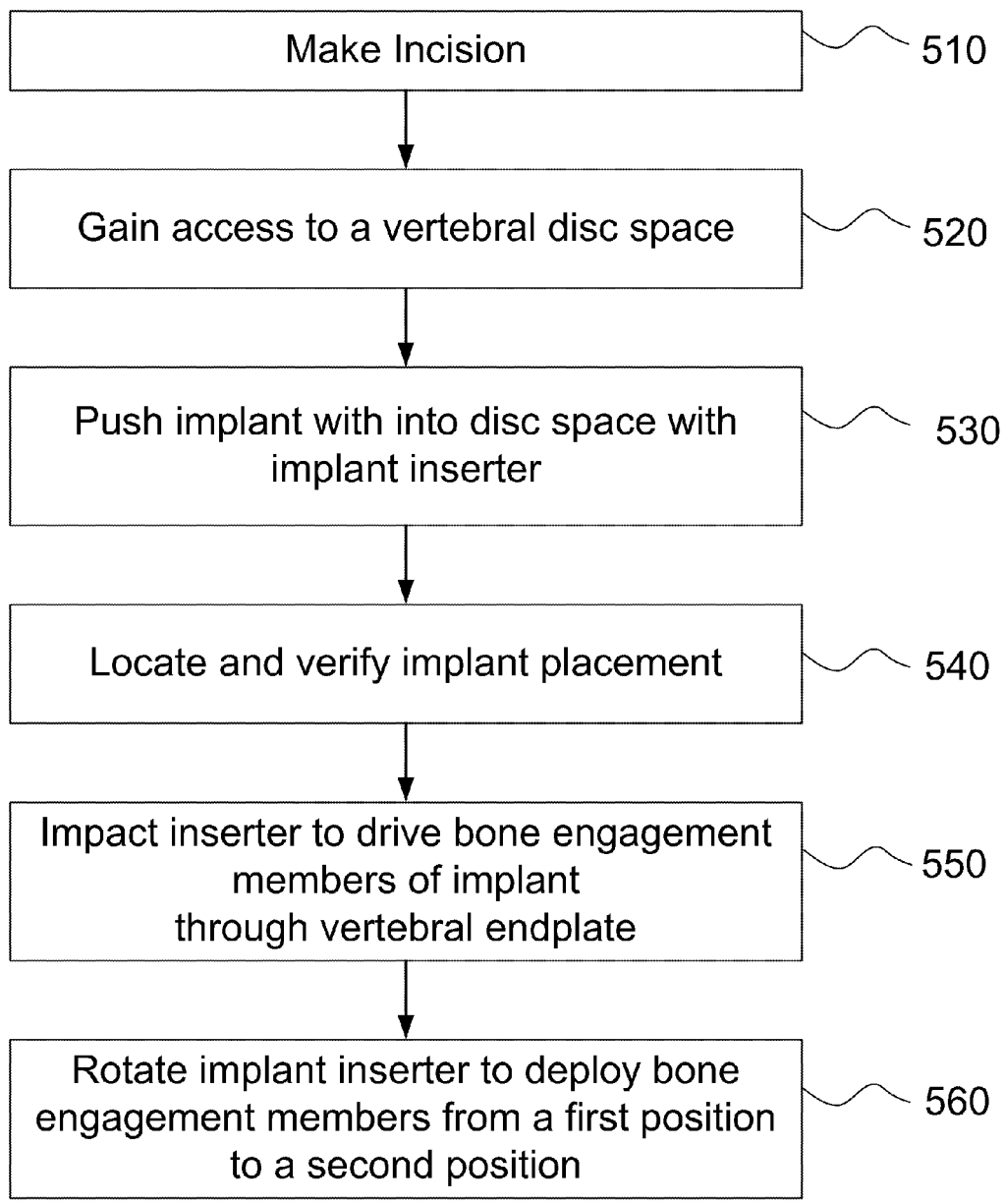
FIG. 9 is a flow diagram of one possible method for inserting the vertebral interbody compression implant of FIG. 1.

Referring to FIG. 9 there is shown a flow diagram of one possible method of inserting the implant 10 between a pair of adjacent vertebrae. A surgeon or technician may make an incision in a patient, as shown in step 510. The incision may be made anteriorly through the patient's abdomen, posteriorly through the patient's back or laterally through the patient's side. It should be noted that even though the implant 10 is described as having a leading end 14 and a trailing end 12, any portion of the device, depending on the technique chosen by the surgeon, may be the portion of the implant 10 that is introduced first into the disc space. The implant 10 may be utilized for an ALIF, PLIF, TLIF or XLIF technique.

The surgeon may use various instruments, such as retractors and rongeurs to gain access to a vertebral disc space (step 520) of the patient's spine. If needed, the surgeon may remove some of the disc space to allow for insertion of an implant 10. As shown in step 530, the surgeon may push the implant 10 having bone engagement members into the disc space with the implant inserter 300. The desired location of the implant may be located and verified 540 through visualization, probes, guides or fluoroscopy.

Figure 10A:
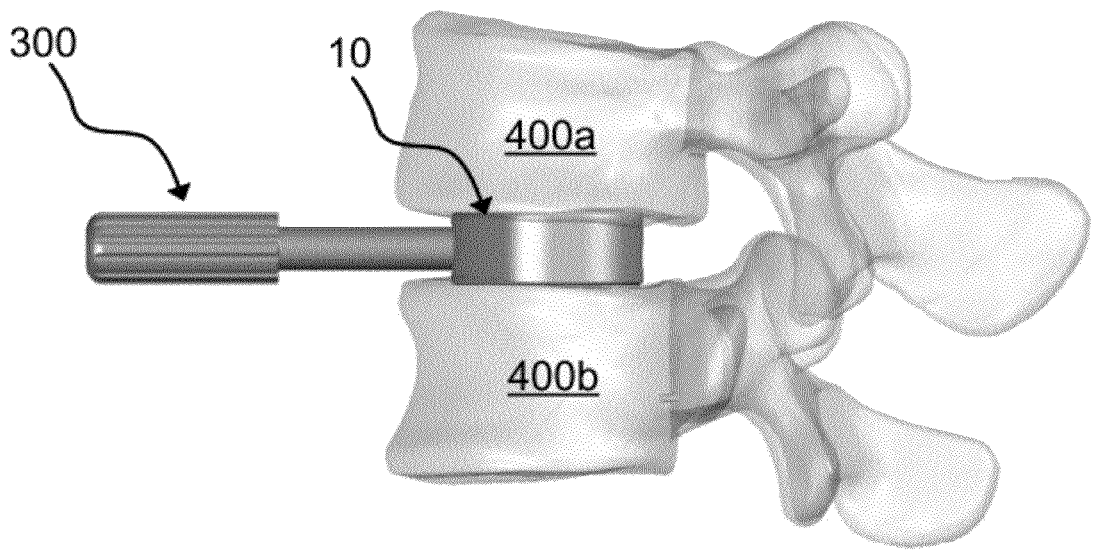
FIG. 10A is a side view of the insertion instrument of FIG. 8 inserting the vertebral interbody compression implant of FIG. 1 between two adjacent vertebrae.
Figure 10B:
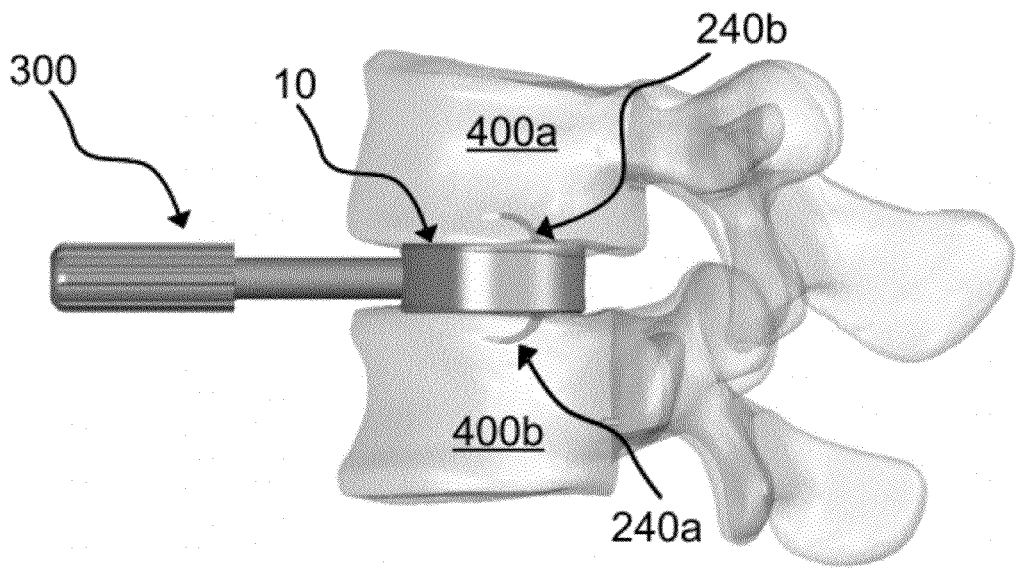
FIG. 10B is a side view of two adjacent vertebrae with the insertion instrument of FIG. 8 and the vertebral interbody compression implant of FIG. 1 in a second position.

Referring briefly to FIGS. 10A and 10B, a side view of the insertion instrument 300 is shown with the implant 10 inserted between two adjacent vertebrae 400a and 400b. Once the desired location is achieved, the surgeon may impact the implant inserter 300 to drive bone the engagement members 240a and 240b of the implant 10 into the vertebrae 400a and 400b. The surgeon may use an instrument, such as a mallet (not shown), to impact the proximal end of the inserter 300 which may move the compression mechanism 200 on the implant 10. The impaction force may cause the ends of the bone the engagement members 240a and 240b to penetrate the vertebrae. As shown in step 560 of FIG. 9 (and in FIG. 10B), the implant inserter 300 may be rotated by use of the handle 310, to deploy the bone engagement members 240a and 240b, as described in FIGS. 7A and 7B, from a first position to a second position in which the vertebrae 400a and 400b may be compressed against the implant 10.

Other embodiments may include the engagement members 240a and 240b that are deployed in opposite directions. For example the bone engagement member 240 may deploy in an anterior direction and the engagement member 240b may deploy in a posterior direction. In FIG. 10B both engagement members 240a and 240b are shown deployed in an anterior direction, but both engagement members 240a and 240b may also be deployed in a posterior direction or a lateral direction.

In certain embodiments the main body 100 and the compression mechanism 200 may be manufactured using conventional manufacturing techniques such as casting, machining, molding or thermoforming. The main body 100 may be manufactured from metals (such as stainless steel or titanium), plastics (such as PEEK or UHMWPE), bone, ceramic, composites or any combination thereof. In certain embodiments the compression mechanism 200 may be manufactured from metals (such as stainless steel or titanium), plastics (such as PEEK or UHMWPE) or a combination.

Although only a few exemplary embodiments of this disclosure have been described in detail above, those skilled in the art will readily appreciate that many modifications are possible in the exemplary embodiments without materially departing from the novel teachings and advantages of this disclosure. Also, features illustrated and discussed above with respect to some embodiments can be combined with features illustrated and discussed above with respect to other embodiments. Accordingly, all such modifications are intended to be included within the scope of this disclosure.

I claim:

1. An implant for securing boney structures, the implant comprising:
 a compression mechanism having bone engagement members slideably coupled to a housing and rotatably coupled to the implant, the housing moveably positioned within the implant, wherein a movement of the housing relative to the implant causes the bone engagement members to slide within the housing and the bone engagement members to rotate away from the implant; and a force transfer mechanism coupled to the compression mechanism and configured to move the housing.

2. The implant of claim 1, the implant further comprising;

a body dimensioned to fit in a disc space between adjacent boney structures, wherein the body comprises a first surface configured to face a first adjacent boney structure, a second surface configured to face a second adjacent boney structure, a passageway in the body extending along a first direction dimensioned to receive the compression mechanism and the force transfer mechanism, an implant slot extending along the passageway on the first surface and the second surface, and wherein the bone engagement members are dimensioned to at least partially pass through the implant slot.

3. The implant of claim 2, wherein the body further comprises a leading end and a trailing end opposite the leading end, wherein the leading end and the trailing end are connected by opposing sides to form a shape to the first surface and second surface that generally conforms with the shape of a vertebral endplate of a spine, wherein reinforcing walls extending through generally the center of the body connect the leading end the trailing end, and wherein the leading end, the trailing end, and the reinforcing walls define the passageway.

4. The implant of claim 3, wherein the leading end, the trailing end, the reinforcing walls define openings in the body that extend from the first face to the second face adjacent to the reinforcing walls, and wherein the openings are configured to receive bone growth material.

5. The implant of claim 1, wherein the engagement members comprise a pair of bone engagement members configured to deploy in an anterior direction relative to adjacent vertebrae.

6. The implant of claim 1, wherein the engagement members comprise a pair of bone engagement members configured to deploy in a posterior direction relative to adjacent vertebrae.

7. The implant of claim 1, wherein the engagement members comprise a pair of bone engagement members configured to deploy in a lateral direction relative to adjacent vertebrae.

8. The implant of claim 1, wherein the bone engagement members are configured for at least a first and a second position, the first position corresponds to the bone engagement members located substantially within the implant, and the second position corresponds to the engagement members fully deployed from the implant for securing the implant to adjacent boney structures.

9. A vertebral interbody compression implant for maintaining the spacing between adjacent bony structures, the implant comprising:

a compression mechanism for securing the implant to the adjacent bony structures, wherein the compression mechanism comprises:

a housing having arm extension members extending along a longitudinal axis in a first direction, wherein the housing is configured to move linearly within a passage in the implant; and bone engagement members comprising bone penetrating elements, wherein the bone engagement members are slideably coupled to the arm extension members and rotatably coupled to the implant, such that a linear movement of the housing causes a tab portion of the bone engagement members to slide within a slot of the arm extension members and the bone penetrating elements to follow an arcuate path away from the implant; and a force transfer mechanism for moving the plurality of bone engagement members, the force transfer mechanism comprising:

a drive shaft coupled to one end of the housing and extending along the longitudinal axis in a second direction opposite the first direction; and a drive element coupled to the drive shaft and configured to apply a force to the housing to move the housing axially in the first direction relative to the drive element to cause the tab of the bone engagement member to slide in the slot and rotate about the first end, wherein the bone engagement members rotate from a first position to a second position.

10. The implant of claim 9, the implant further comprising:

a body dimensioned to fit in a disc space between adjacent boney structures, wherein the body comprises a first surface configured to face a first adjacent boney structure, a second surface configured to face a second adjacent boney structure, and wherein the body may be configured to receive the compression mechanism and the force transfer mechanism in the passage.

11. The implant of claim 10, wherein the body further comprises a leading end and a trailing end opposite the leading end, wherein the leading end and the trailing end are connected by opposing sides to form a shape of the first surface and the second surface that generally conforms with a shape of a vertebral endplate, wherein reinforcing walls extending through generally the center of the body connect the leading end the trailing end, and wherein the reinforcing walls form the passage.

12. The implant of claim 9, wherein the drive element is configured to threadably engage a threaded cylindrical shaft of the drive shaft, wherein the drive element may be advanced along the drive shaft by a force transfer member, and wherein the force transfer member comprises an outer surface configured to transfer a force to move the housing axially in the first direction.

13. The implant of claim 12, wherein the drive element further comprises a shoulder configured to make contact with a surface of the implant to prevent the compression mechanism from advancing along the drive shaft.

14. The implant of claim 13, wherein the force transfer member is configured to receive a torque from an inserter, and wherein the inserter comprises a shaft coupled to a handle at a proximal end for turning the shaft, the handle further having an impaction surface for receiving a blunt force, and, at a distal end of the shaft, a surface defining a torque transfer element.

15. A vertebral interbody compression implant for maintaining the spacing between adjacent boney structures, the implant comprising:

a compression mechanism for securing the implant to the adjacent bony structures, wherein the compression mechanism comprises:

a housing configured to slide along a passageway in the implant, the housing having a first arm extension and a second arm extension that extend in a first direction along a longitudinal axis in the passageway within the implant, wherein the first arm extension and the second arm extension form a channel, and wherein the first arm extension and the second arm extension comprise a first slot and second slot that extend in a generally transverse direction relative to the longitudinal axis and that are opposing across the channel;

a first bone engagement member comprising a first arm extending from a first tab slidingly coupled to the housing in the first slot to a first end rotatably coupled to the implant, and a second arm extending from the first tab to a second end having a bone penetrating element for piercing adjacent bony structures, wherein the second arm is configured to rotate away from a first side of the implant towards a first adjacent boney structure;

a second bone engagement member comprising a first arm extending from a second tab slidingly coupled to the housing in the second slot to a first end rotatably coupled to the implant, and a second arm extending from the second tab to a second end having a bone penetrating element for piercing adjacent bony structures, wherein the second arm is configured to rotate away from a second side of the implant towards a second adjacent boney structure; and wherein a force applied to the housing by a force transfer mechanism coupled to the housing moves the housing longitudinally in the passageway in the first direction to slide the first tab of the first bone engagement member within the first slot and the second tab of the second bone engagement member within the second slot in generally the opposite direction as the first tab, and to rotate the second arm of the first bone engagement member and the second bone engagement member about the first end in generally opposite directions away from the implant, wherein the first bone engagement member and the second bone engagement member rotate from a first position to a second position.

16. The implant of claim 15, wherein the second arm of the first bone engagement member and the second arm of the second bone engagement member comprise respective curved members configured to deploy along respective curved paths for compressing adjacent boney structures.

17. The implant of claim 15, wherein the first position corresponds to the housing being located adjacent to a drive element of the force transfer mechanism and the bone penetrating element of the first bone engagement member and the bone penetrating element of the second bone engagement member are located substantially within the implant, and wherein the second position corresponds to the housing being located distal to the drive element of the force transfer mechanism and the bone penetrating element of the first bone engagement member and the bone penetrating element of the second bone engagement member protruding out of the implant.

* * * * *